(12) United States Patent
De Lima Vasconcellos et al.

(10) Patent No.: US 9,879,285 B2
(45) Date of Patent: Jan. 30, 2018

(54) PRODUCTION OF BIOGAS FROM ORGANIC MATERIALS

(71) Applicant: ANAERGIA INC., Burlington (CA)

(72) Inventors: Marcelo De Lima Vasconcellos, Erding (DE); Juan Carlos Josse, Mission Viejo, CA (US)

( * ) Notice: Subject to any disclaimer, the term of this patent is extended or adjusted under 35 U.S.C. 154(b) by 0 days.

(21) Appl. No.: 15/085,381

(22) Filed: Mar. 30, 2016

(65) Prior Publication Data

US 2017/0022522 A1    Jan. 26, 2017

Related U.S. Application Data

(60) Provisional application No. 62/194,471, filed on Jul. 20, 2015.

(51) Int. Cl.

| | | |
|---|---|---|
| *C12P 3/00* | (2006.01) | |
| *C02F 11/04* | (2006.01) | |
| *B03B 5/34* | (2006.01) | |
| *B03B 9/06* | (2006.01) | |
| *B09B 3/00* | (2006.01) | |
| *C05F 9/04* | (2006.01) | |
| *B09B 5/00* | (2006.01) | |
| *C12M 1/107* | (2006.01) | |
| *C12M 1/33* | (2006.01) | |

(52) U.S. Cl.
CPC ...... *C12P 3/00* (2013.01); *B03B 5/34* (2013.01); *B03B 9/06* (2013.01); *B09B 3/00* (2013.01); *B09B 5/00* (2013.01); *C05F 9/04* (2013.01); *C12M 21/04* (2013.01); *C12M 45/02* (2013.01); *C02F 11/04* (2013.01); *C02F 2209/03* (2013.01); *C02F 2303/24* (2013.01); *Y02P 20/145* (2015.11); *Y02W 30/20* (2015.05); *Y02W 30/47* (2015.05); *Y02W 30/524* (2015.05)

(58) Field of Classification Search
CPC ..... C12P 3/00; B03B 5/34; B03B 9/06; B03B 3/00; B03B 5/00; C02F 11/04; C02F 2209/03; C02F 2303/24; C12M 21/04; C12M 45/02
USPC ....................... 210/603, 608, 609
See application file for complete search history.

(56) References Cited

U.S. PATENT DOCUMENTS

| | | |
|---|---|---|
| 4,289,625 A | 9/1981 | Tarman et al. |
| 4,880,473 A | 11/1989 | Scott et al. |
| 5,017,196 A | 5/1991 | Dewitz |

(Continued)

FOREIGN PATENT DOCUMENTS

| | | |
|---|---|---|
| BR | 9401102 A | 11/1994 |
| CA | 2628323 A1 | 6/2007 |

(Continued)

OTHER PUBLICATIONS

ASTM, Section D3172, Proximate Analsys of Coal and Coke, Oct. 1, 2007, 2 pages.

(Continued)

*Primary Examiner* — Fred Prince

(57) ABSTRACT

Waste or organic material is compressed at a pressure sufficient to burst cells, for example 50 bar or more, and separated into a dry fraction and a wet fraction. The wet fraction is treated in an anaerobic digester to produce biogas after removing grit. The wet fraction is diluted, preferably with sludge, before it is degritted. Optionally, floatables are removed from the fraction before it is added to the digester.

13 Claims, 4 Drawing Sheets

(56) References Cited

U.S. PATENT DOCUMENTS

| | | | |
|---|---|---|---|
| 5,395,455 | A | 3/1995 | Scott et al. |
| 5,417,492 | A | 5/1995 | Christian et al. |
| 5,424,417 | A | 6/1995 | Torget et al. |
| 5,605,551 | A | 2/1997 | Scott et al. |
| 5,865,898 | A | 2/1999 | Holtzapple et al. |
| 5,959,167 | A | 9/1999 | Shabtai et al. |
| 6,022,419 | A | 2/2000 | Torget et al. |
| 6,048,374 | A | 4/2000 | Green |
| 6,228,177 | B1 | 5/2001 | Torget |
| 7,229,483 | B2 | 6/2007 | Lewis |
| 7,494,637 | B2 | 2/2009 | Peters et al. |
| 7,578,927 | B2 | 8/2009 | Marker et al. |
| 7,608,439 | B2 | 10/2009 | Offerman et al. |
| 7,972,824 | B2 | 7/2011 | Simpson et al. |
| 8,383,871 | B1 | 2/2013 | Sellars et al. |
| 8,877,468 | B2 | 11/2014 | Lewis |
| 8,993,288 | B2 | 3/2015 | Lewis |
| 2004/0084366 | A1 | 5/2004 | Anderson et al. |
| 2006/0112639 | A1 | 6/2006 | Nick et al. |
| 2006/0289356 | A1 | 12/2006 | Burnett et al. |
| 2007/0117195 | A1 | 5/2007 | Warner et al. |
| 2007/0217995 | A1 | 9/2007 | Matsumura et al. |
| 2008/0035561 | A1 | 2/2008 | Gray |
| 2008/0236042 | A1 | 10/2008 | Summerlin |
| 2008/0280338 | A1 | 11/2008 | Hall et al. |
| 2009/0151253 | A1 | 6/2009 | Manzer et al. |
| 2009/0229595 | A1 | 9/2009 | Schwartz, Jr. |
| 2009/0239279 | A1 | 9/2009 | Hall et al. |
| 2010/0021979 | A1 | 1/2010 | Facey et al. |
| 2010/0133085 | A1 | 6/2010 | Hutchins et al. |
| 2010/0162627 | A1 | 7/2010 | Clomburg, Jr. et al. |
| 2010/0223839 | A1 | 9/2010 | Garcia-Perez et al. |
| 2010/0317070 | A1 | 12/2010 | Agaskar |
| 2011/0033908 | A1 | 2/2011 | Cheong et al. |
| 2011/0179700 | A1 | 7/2011 | Monroe et al. |
| 2011/0248218 | A1 | 10/2011 | Sutradhar et al. |
| 2012/0073199 | A1 | 3/2012 | Lewis |
| 2012/0322130 | A1 | 12/2012 | Garcia-Perez et al. |
| 2013/0134089 | A1* | 5/2013 | Cote .................. C02F 3/30 210/605 |
| 2013/0316428 | A1 | 11/2013 | Gonella |

FOREIGN PATENT DOCUMENTS

| | | | |
|---|---|---|---|
| CA | 2641270 | A1 | 12/2009 |
| DE | 10107712 | A1 | 9/2002 |
| EP | 0521685 | A2 | 1/1993 |
| EP | 1207040 | A2 | 5/2002 |
| EP | 1568478 | A1 | 8/2005 |
| GB | 1571886 | A | 7/1980 |
| GB | 2257137 | A * | 1/1993 |
| GB | 2332196 | A * | 6/1999 |
| JP | 2003089793 | A | 3/2003 |
| WO | 0179123 | A1 | 10/2001 |
| WO | 2004060587 | A1 | 7/2004 |
| WO | WO 2006/056620 | A1 * | 6/2006 |
| WO | 2010001137 | A2 | 1/2010 |
| WO | 2012166771 | A2 | 12/2012 |
| WO | 2013110186 | A1 | 8/2013 |
| WO | 2015050433 | A1 | 4/2015 |
| WO | 2015053617 | A1 | 4/2015 |

OTHER PUBLICATIONS

AWWTA, Standard Methods, Section 240G, (2000).
Bredwell et al., "Reactor Design Issues for Synthesis-Gas Fermentations, Biotechnology Process," Biotechnology Process, 1999, vol. 15 (5), pp. 834-844.
Cozzani et al., "A Fundamental Study on Conventional Pyrolysis of a Refuse-Derived Fuel," Industrial & Engineering Chemistry Research, Jun. 1995, 34, pp. 2006-2020.
Demirbas et al., "Biomass Resource Facilities and Biomass Conversion Processing for Fuels and Chemicals," Energy Conversion and Management, Jul. 2001, vol. 42 (11), pp. 1357-1378.
Demirbas et al., "The Influence of Temperature on the Yields of Compounds Existing in Bio-Oils Obtained from Biomass Samples via Pyrolysis," Fuel Processing Technology, Jun. 2007, vol. 88 (6), pp. 591-597.
European Patent Application No. 13740592, Supplementary European Search Report dated Jul. 27, 2015.
European Patent Application No. 16162806, Extended European Search Report dated Dec. 14, 2016.
Excerpts from Traite De Polarimetrie, Georges Bruhat, Paris, France, 1930.
Garcia-Perez, "Challenges and Opportunities of Biomass Pyrolysis to Produce Second Generation Bio-fuels and Chemicals," Auburn University, Jun. 13, 2012, 66 pages.
Guiot et al., "Potential of Wastewater-Treating Anaerobic Granules for Biomethanation of Synthesis Gas," Environmental Science and Technology, Mar. 2011, vol. 45 (5), pp. 2006-2012.
Gullu et al., "Biomass to Methanol via Pyrolysis Process," Energy Conversion and Management, Jul. 2001, vol. 42 (11), pp. 1349-1356.
International Patent Application No. PCT/CA2013/050037, International Preliminary Report on Patentability dated Aug. 7, 2014.
International Patent Application No. PCT/CA2013/050037, International Search Report dated Apr. 4, 2013.
International Patent Application No. PCT/CA2014/050662, International Preliminary Report on Patentability dated Jan. 12, 2016.
International Patent Application No. PCT/CA2014/050662, International Search Report and Written Opinion dated Sep. 25, 2014.
Jenkins, "Oxidation-Based Water-Reuse Technology that Improves Mass Transfer," Chemical Engineering, Feb. 2013, p. 12.
Jones, et al., "Production of Gasoline and Diesel from biomass via Fast Pyrolysis" Hydrotreating and Hydrocracking: A Design Case, U.S. Department of Energy, PNNL-18284 Feb. 28, 2009, 76 pages.
Laemsak, "Wood Vinegar Presentation," Undated, 5 pages.
Laird et al., "Sustainable Alternative Fuel Feedstock Opportunities, Challenges and Roadmaps for Six U.S. Regions," Chapter 16: Pyrolysis and Biochar—Opportunities for Distributed Production and Soil Quality Enhancement, Proceedings of the Sustainable Feedstocks for Advance Biofuels Workshop, Atlanta, GA, Sep. 28-30, 2010, pp. 257-281.
Lehmann et al., "Bio-Char Sequestration in Terrestrial Ecosystems—A Review ," Mitigation and Adaptation Strategies for Global Change , Mar. 2006, vol. 11 (2), pp. 403-427.
Yang et al., "Pretreatment: The Key to Unlocking Low-Cost Cellulosic Ethanol," Biofuels, Bioproducts and Biorefinering, Jan. 2008, vol. 2 (1), pp. 26-40.
Lian et al., "Separation, Hydrolysis and Fermentation of Pyrolytic Sugars to Produce Ethanol and Lipids," Bioresource Technology, Dec. 2010, vol. 101 (24), pp. 9688-9699.
Liaw et al., "Effect of Pyrolysis Temperature on the Yield and Properties of Bio-oils Obtained From the Auger Pyrolysis of Douglas Fir Wood," Journal of Analytical and Applied Pyrolysis, Jan. 2012, vol. 93, pp. 52-62.
Linden et al., "Gaseous Product Distribution in Hydrocarbon Pyrolysis," Industrial and Engineering Chemistry, 1955, vol. 47 (12), pp. 2470-2474.
Mahulkar et al., "Steam Bubble Cativation," AIChE Journal, Jul. 2008, vol. 54 (7), pp. 1711-1724.
Melin et al., "Evaluation of Lignocellulosic Biomass Upgrading Routes to Fuels and Chemicals," Cellulose Chemistry and Technology, 2010, vol. 44 (4-6), pp. 117-137.
Parry, Biosolids Technology Advances, Jan. 2012, 20 Pages.
Parry, et al. "Prolysis of Dried Biosolids for Increased Biogas Production" Proceedings of the Water Environment Federation, Residuals and Biosolids, Mar. 2012, pp. 1128-1139.
Zhang et al., "Influence of Manure Types and Pyrolysis Conditions on the Oxidation Behavior of Manure Char," Bioresource Technology, Sep. 2009, vol. 100 (18), pp. 4278-4283.
Shanley Pump and Equipment, Inc., EDUR Pumps, [online], printed May 30, 2014. Retrieved from the Internet.
Smith et al., "Integrating Pyrolysis and Anaerobic Digestion," The Northwest Bio-energy Symposium, Seattle, Washington, Nov. 13, 2012, 44 pages, http://www.pacificbiomass.org/documents/Smith.pdf.

(56) References Cited

OTHER PUBLICATIONS

Sustarsic, "Wastewater Treatment: Understanding the Activated Sludge Process" CEP Nov. 2009, pp. 26-29.
U.S. Appl. No. 13/826,507, Advisory Action dated May 22, 2015.
U.S. Appl. No. 13/826,507, Notice of Allowance dated Sep. 29, 2016.
U.S. Appl. No. 13/826,507, Office Action dated Feb. 26, 2016.
U.S. Appl. No. 13/826,507, Office Action dated Jul. 7, 2014.
U.S. Appl. No. 13/826,507, Office Action dated Mar. 18, 2015.
U.S. Appl. No. 13/826,507, Restriction Requirement dated Apr. 11, 2014.
U.S. Appl. No. 14/373,714, Notice of Allowance dated Feb. 10, 2016.
U.S. Appl. No. 14/373,714, Office Action dated Jul. 24, 2015.
Vit et al., English language abstract of DE10107712, published Sep. 5, 2002.
Water and Sewage Treatment Energy Management Joint Conference, Delaware Valley Regional Planning Commission, Apr. 25, 2012, 55 Pages.
Written Opinion for Application No. PCT/CA2013/050037, dated Apr. 4, 2013, 7 pages.

\* cited by examiner

PRODUCTION OF BIOGAS FROM ORGANIC MATERIALS

CROSS-REFERENCE TO RELATED APPLICATIONS

This application is a non-provisional application of U.S. Application Ser. No. 62/194,471, filed Jul. 20, 2015, which is incorporated herein by reference.

FIELD

This specification relates to treating waste or organic material and biogas production.

BACKGROUND

US Publication 2013/0316428 describes a process in which an organic fraction containing biological cells is separated from solid urban waste. The organic fraction is extruded through a grid having small-bore holes, under a pressure higher than the burst pressure of the cell membranes. The cells are disrupted and a gel of a doughy consistency is produced. The gel is then loaded into a biodigester, where it is readily attacked by bacteria. The press may be as described in European Publication Nos. 1207040 and 1568478. In general, these presses use a plunger to compress waste that has been loaded into a cylinder. The sides of the cylinder are perforated with radial holes. US Publication 2013/0316428 and European Publication Nos. 1207040 and 1568478 are incorporated herein by reference.

INTRODUCTION TO THE INVENTION

This specification describes a process and apparatus for treating organic or waste material to produce biogas. The material may be, for example, municipal solid waste (MSW), an organic fraction of municipal solid waste such as source-separated organics or commercial and/or industrial waste (C&I) such as food processing or grocery waste. Mixtures of one or more of these materials may also be used.

In a process, the waste or organic material is pressed at a pressure sufficient to burst cells, for example 50 bar or more, and separated into a dry fraction and a wet fraction. The wet fraction is treated in an anaerobic digester to produce biogas. Digestate (digester sludge) is also produced and may be used, for example, as land-applied fertilizer or to make compost.

The wet fraction is preferably processed before it is treated in the anaerobic digester. Particularly when the material being pressed is municipal solid waste, the liquid fraction will have floatables such as small bits of plastic films or bags, paper and fibers. If not removed, the floatables can accumulate in the digester or become part of the digestate or both. Although there may be only a small amount of floatables, for example 1 to 1.5% by mass (wet basis) of the wet fraction produced by the press, having them in the digestate may prevent disposing of digestate by land application or using the digestate for compost. For example, California standards for digestate land application and composting require physical contaminants larger than 4 mm to be no more than 0.1% of the digestate on a wet basis. The floatables may be removed if required from the digestate. Preferably, floatables are removed from the wet fraction in a plastics separator, preferably a dynamic cyclone. Having been removed from the wet fraction, the floatables are not present in excessive amounts in the digestate.

Although the press does not create grit like a hammer mill or pulper, the wet fraction still contains grit, which can settle in the digester as the wet fraction is decomposed. Grit settling is a particular problem when the wet fraction is co-digested with wastewater treatment plant (WWTP) sludge since the resulting digestate has lower solids content and viscosity and WWTP digesters are not typically designed to handle much settled grit. However, sufficient grit removal cannot be obtained by gravity settling of the wet fraction since its viscosity is too high. In a process described herein, the wet fraction is diluted but only as required for the grit removal device, which is preferably selected to accept high solids feed. For example, a hydro-cyclone is able to process the wet fraction after dilution to 8 to 12% total solids (TS), preferably 10-12% TS, since the action of the hydro-cyclone lowers the effective viscosity of the wet fraction. The grit is preferably rinsed after being removed from the wet fraction so make it more suitable for disposal and to recover more of the organics.

The wet fraction may be diluted for grit removal with a filtrate or other relatively clean source of water, for example filtrate from digestate dewatering. However, to conserve water and avoid diluting the digester, the wet fraction is preferably diluted with sludge. The inventors have observed that, since the wet fraction is very high in volatile solids, it produces digestate with much-reduced solids content. The wet fraction can therefore be diluted with digestate drawn from the anaerobic digester. Alternatively, in a case where the digester is located in a wastewater treatment plant (WWTP) and co-digests WWTP sludge, the wet fraction may be diluted with waste activated sludge or primary sludge from the wastewater treatment plant. In this case, the WWTP sludge is also de-gritted before being added to the anaerobic digester.

Grit removal preferably follows floatables removal if floatables are removed upstream of the digester. The floatables removal can occur without dilution and effective throughput would be reduced if floatables were removed from diluted wet fraction. Similarly, removing flotables from the wet fraction rather than from digestate is preferred because it improves effective throughput. Grit removal is also performed on minimally diluted wet fraction, rather than for example digestate recirculating in a side stream loop, to also provide better effective throughput. In general, the invention provides very compact treatment by selecting unit processes able to handle high solids feed and operating the unit process at or near their maximum solids tolerance.

The specification also describes an apparatus suitable for the processes described above.

DETAILED DESCRIPTION

Figure 1:
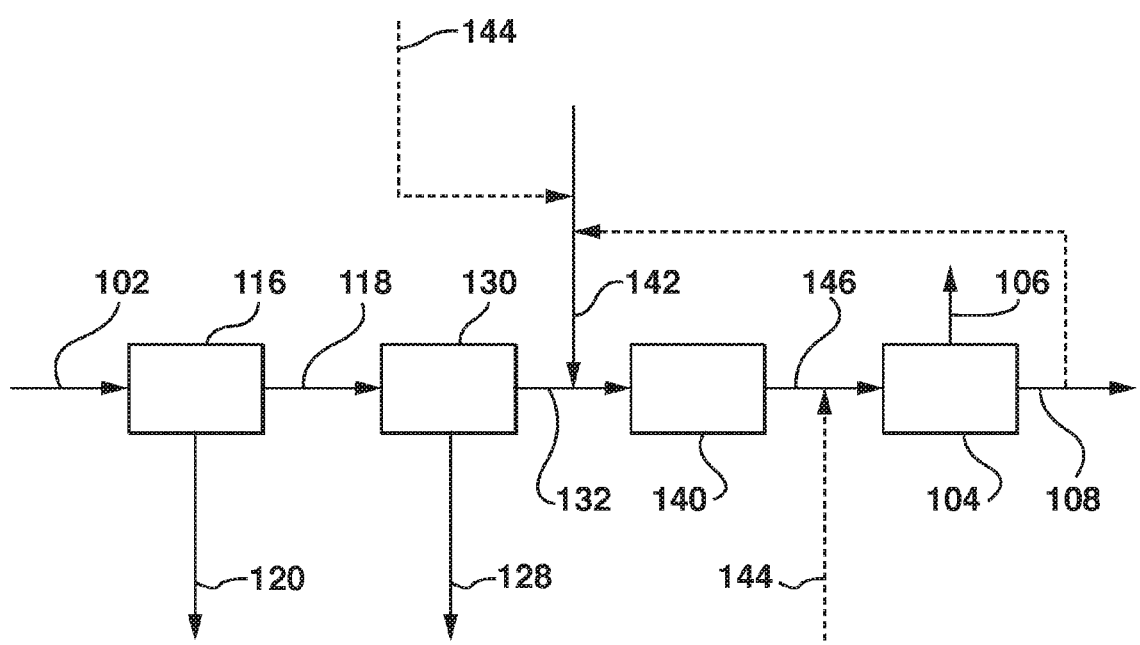
FIG. 1 is a process flow diagram of a process for treating waste or organic material.

FIG. 1 shows a system 100 for treating a feed stream 102 of waste or organic materials. The feed stream 102 may be, for example, municipal solid waste (MSW), MSW separated to isolate an organic fraction for treatment, i.e. source-separated organics (SSO), commercial and/or industrial waste (C&I), or a mixture of one or more of these of other wastes. Optionally, plastics, and other typically non-digestable hydrocarbon materials such as wood, may be left in the waste. Metals and mineral waste are preferably removed.

The feed stream 102 flows into a press 116. The press 116 compresses the feed 102 at high pressure through small perforations. For example, the pressure may be at least 50 bar or otherwise sufficient to rupture biological cells. The perforations may be, for example, 4 to 8 mm diameter circular holes. The press 116 separates the feed 102 into a wet fraction 118 and a dry fraction 120. The wet fraction 118 contains soluble organic compounds, including organics contained in cells ruptured under high pressure. Preferably, 95% or more of the organics in feed stream 102 is contained in the wet fraction 118.

The wet fraction 118 is sent to an anaerobic digester 104, optionally referred to as digester 104 for brevity, to produce biogas 106. The anaerobic digester 104 also produces digestate 108 which may be treated further, for example to produce a process fertilizer or recover ammonia, used directly as fertilizer by land application, or used to produce compost. Although the term digestate is sometimes used to refer specifically to a dry fraction of anaerobic digester sludge, in this specification the term digestate refers to the anaerobic digester sludge generally.

The wet fraction 118 typically has a 20-35% solids content, 20-25% from wet commercial waste; 30-35% from residential MSW. The wet fraction 118 also typically has a 85-95% volatile solids to total solids ratio. The wet fraction 118 may be 30-40% of the feed stream 102 when pressing MSW, or 70-85% of the feed stream 102 when pressing SSO.

The wet fraction 118 from the press is preferably treated before it is sent to the digester. The wet fraction 118 includes floatables, such as pieces of plastic films, foils or bags, that pass through the perforations of the press 116. The wet fraction 118 also contains grit, small particles of inorganic or recalcitrant material that will be difficult or impossible to digest.

In a first step, the wet fraction 118 is treated to remove floatables in a plastics separator 130. In the plastics separator 130, the wet fraction 118 is fed into a screen cylinder surrounding a rotor. Particles of organic matter in the wet fraction 118 are flung outward from a rotor by its rotating movement and centrifugal forces. The particles of organic material are discharged through perforations in the screen to a first discharge opening. Air flowing along the axis of the rotor carries lighter material past the perforations to a second discharge opening. The air flow may be created by the rotor blades or by a separate fan. The rotor blades may optionally also scrape the inside of the screen. In this way, lighter particles (particularly bits of plastic) are separated from the organic particles in the liquid fraction 118. The plastics separator thereby produces separated organic material 132 and become separated plastic 128. Preferably, at least 90% of the floatables in the wet fraction 118 are removed in the plastics separator 130.

In a second step, the separated organic material 132 is treated in a grit removal unit 140. Although the wet fraction 118 (and separated organic material 132) may have a very high solids content, it is highly volatile and produces digestate with moderate solids content. For example, wet fraction with 25% solids content may produce digestate with a solids content of only 6%. At 6% solids, the digestate is still viscous enough to suspend small (i.e. 2-3 mm grit particles) but larger grit particles will settle in the digester. However, it is advantageous to co-digest the wet fraction with WWTP sludge since WWTP digesters 104 often have excess capacity and would perform better at a higher loading rate. When co-digesting, the solids content in the digester 104 is reduced, for example to about 3% solids. At this solids content, even 2-3 mm grit particles will settle in the digester 104.

The grit removal unit 140 preferably includes a hydro-cyclone. A hydro-cyclone is typically able to process feed at about 8-12% solids. A dilutant 142 is added to the separated organic material 132 to bring its solids content below, but preferably within 2% of, the maximum solids content accepted by the grit removal unit. When the wet fraction 118 is digested in a dedicated digester, the digestate 108 may have, for example 6% solids. When wet fraction 118 is co-digested with WWTP sludge 144, the digestate may have for example 3% solids. Accordingly, the digestate 108 can be used to provide some or all of the diluent 142 in either case. When co-digesting the wet fraction 118 with WWTP sludge 114, some or all of the WWTP sludge 144 can be mixed with the wet fraction 118 (separated organic material 132) for dilution before it is sent to the grit removal unit 140. For example, waste activated sludge (WAS) typically has only about 1-2% solids. Degritted feedstock 146 is sent to the digester 104. Preferably, at least 85% of the grit in the separated organic material 132 is removed in the grit removal unit 140.

In some cases, a small amount of dilution of the wet fraction 118 may be required before it is fed to the plastics separator 130. In these cases, the wet fraction 118 may be diluted as described for the grit removal unit 140.

The dry fraction 120 and separated plastics 128 may be landfilled or used as refuse derived fuel (RDF).

Figure 2:
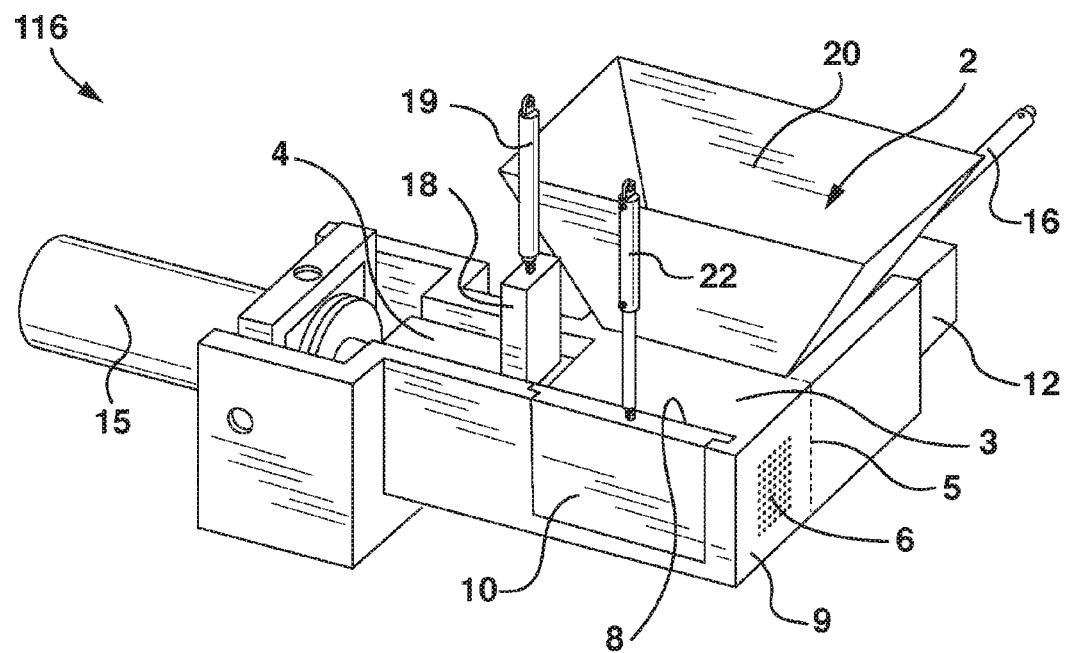
FIG. 2 is an isometric drawing of a press.

FIG. 2 shows an example of a press 116. The press 116 has a first inlet opening 2 located at the bottom of a funnel 20 for receiving the waste or organic material. Material that falls through the first inlet opening 2 can be moved through a second inlet opening 5 into a compression chamber 3 by a second piston 12. The second piston 12 moves from a retracted position outside of the first inlet opening 2 to an intermediate position at the second inlet opening 5. When in the intermediate position, the second piston 12 provides one wall of the compression chamber 3. The second piston 12 is moved by a second hydraulic cylinder 16. Preferably, pins or another mechanism (not shown) are provided to selectively lock the second piston 12 in its intermediate position.

Material in the compression chamber 3 may be compressed by a first piston 4. The compression chamber 3 has perforations 6 arranged in a wall 9 of the compression chamber 3. Optionally, perforations 6 may also be provided in, or associated with, the first piston 4. Perforations 6 allow air and a wet fraction of the material, typically containing water, and fine solids entrained in the water, to leave the compression chamber 3. A tray, not shown, collects the wet fraction.

The first piston 4 is pushed by means of a drive mechanism, for example a first hydraulic cylinder 15. The first piston 4 is movable between retracted and advanced positions. In a retracted position, as shown, the face of the first piston 4 is located just outside of the stroke of second piston 12. In an advanced position, not shown, the piston 4 is located within the compression chamber 3. As the first piston 4 moves from the retracted position towards an advanced position, it compresses sludge in the compression chamber 3. The first piston 4 may move through a pre-determined stroke selected to provide a desired pressure, or the first piston 4 may move until a pre-determined minimum pressure is indicated by a sensor.

The compression chamber 3 also has an outlet 8 for removing a dry fraction of the material from the compression chamber 3. The outlet 8 can be selectively closed by a door 10, here a sliding door driven by a third hydraulic cylinder 22. When closed, the door 10 defines a side of the compression chamber 3. After sludge has been compressed, the door 10 is raised. The second piston 12 then moves through the compression chamber 3 in a direction perpendicular to the stroke of the first piston 4 to an advanced position. In the advanced position, the face of the second piston 12 moves at least to the outside edge of door 10. This ejects a dry fraction of the sludge through the outlet 8. A conveyor belt or auger, not shown, receives the dry fraction.

To compress a volume of material, the first piston 4 and the second piston 12 are both retracted and the door 10 is closed. The volume of material is dropped into the press 116 through funnel 20 and first inlet 2. The second plunger 12 moves to its intermediate position and is locked in this position. This moves the material into the compression chamber 3. The first piston 4 then moves into the compression chamber 3. This compresses the material and separates it into a dry fraction and a wet fraction. The first piston 4 then moves back to its retracted position. Door 10 is opened. The second piston 12 is unlocked and moved to its advanced position. This ejects the dry fraction through the outlet 8. The process can then be repeated to compress another volume of material.

In the press 116 shown, the first piston 4 has perforations through its face and a plenum behind its face. These are optional features and not visible in FIG. 1. A fourth hydraulic cylinder 19 can connect to and lift a receptacle 18 from the plenum to discharge part of the wet fraction of the sludge that accumulates in the receptacle 18.

The perforations 6 preferably have a size of 10 mm or less, for example between 5 mm and 8 mm. For round perforations 6, the size is the diameter. For square perforations 6, the size is the distance between two parallel sides of the square. For perforations 6 of other shapes, the size is determined as the diameter of a circle having the same area.

The material is preferably compressed to a pressure at least sufficient to break open the cells of plants and microorganisms to release the water inside of the cells. This pressure may be about 50 bar. However, a higher pressure, up to about 280 or 300 bar may also be used and may result in higher solids content in the dry fraction.

In use, the press 116 receives feed stream 102 into the funnel 20. The material falls from the funnel 20 and is positioned in the compression chamber 3. The material is compressed and the wet fraction escapes through the perforations 6 leaving the dry fraction temporarily in the compression chamber.

The press 116 shown in FIG. 2 is further described in International Publication Number WO 2015/053617, Device and Method for Pressing Organic Material Out of Waste, which is incorporated herein by reference. A similar press is sold by DB Technologies. Another suitable press is the commercially available VM Press. Other high-pressure presses may also be used.

Figure 3:
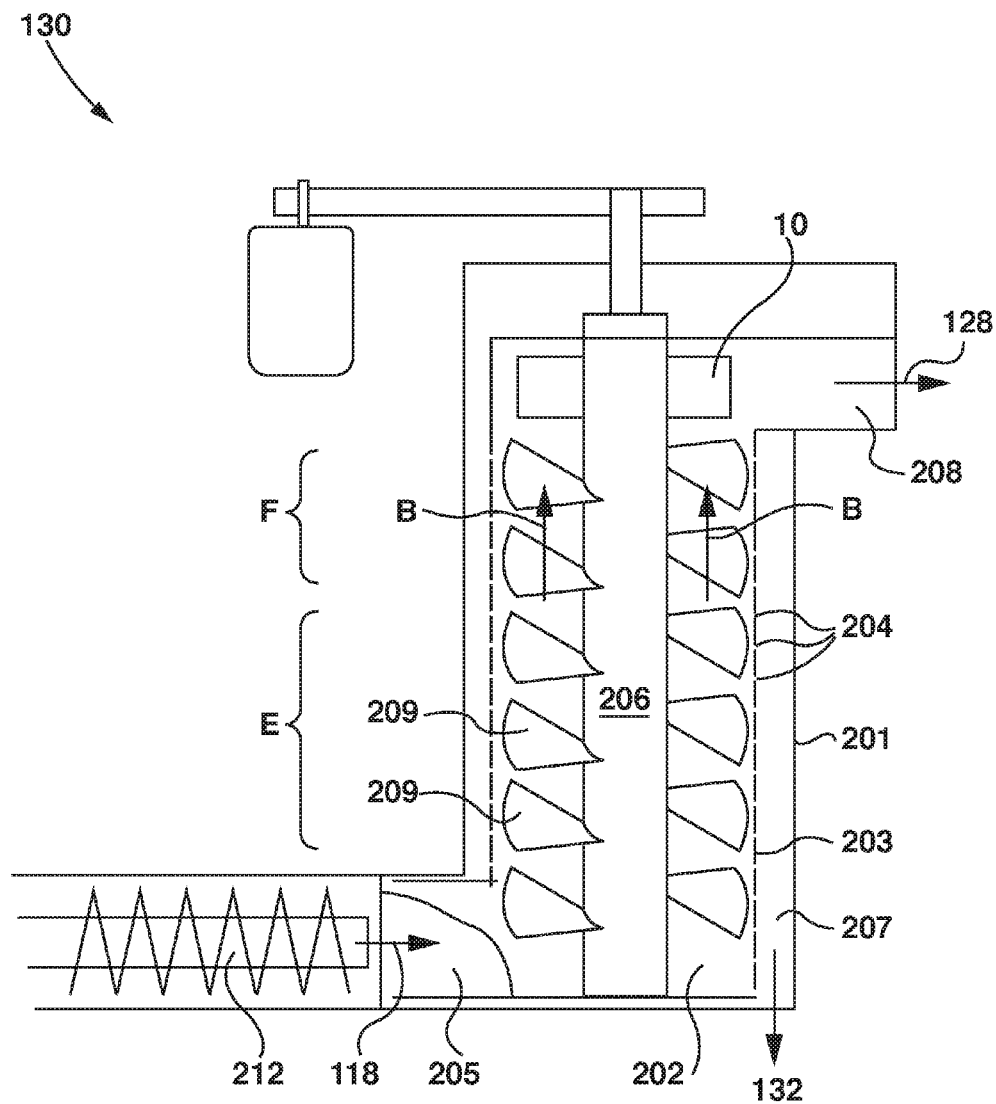
FIG. 3 shows a cross section of a plastics separator.

FIG. 3 shows an example of a plastics separator 130. The plastics separator 130 has a cylindrical housing 201 having therein a cylindrical chamber 202. The wall 203 of the cylindrical chamber 202 has perforations 204, for example circular holes of about 5 mm in diameter. A feed opening 205 admits the liquid fraction 118 conveyed by auger 212. There is also a first discharge opening 207 for discharging separated organic material 132 and a second discharge opening 208 for discharging separated plastic 128. A rotor 206 rotates at a speed of, for example, over 500 rpm, which is sufficient to create, for example, over 150 G of centrifugal force. Rotor 206 has a plurality of first blades 209, which have a pitch upwards. The rotor 206 also has second blades 210, which are generally parallel to the axis of the rotor 206 and located near the second discharge opening 208. Second discharge opening 208 is oriented tangentially to the outer circumference of second blades 210.

In use, liquid fraction 118 is introduced into chamber 202 by auger 212 through feed opening 205. Inside of chamber 202, first blades 209 fling the liquid fraction upwards and outwards against the wall 203. First blades 209 also generate a first airflow B, for example at a speed of 15 m/s and 4000 $m^3/h$. Particles of organic matter and water are flung out through perforations 204 and form separated organic material 132. The particles may deform as they pass through the perforations 204. Lighter plastic particles are carried by first airflow B and then blown out by second blades 210 and become separated plastic 128. Organic particles are mainly flung out through perforations 204 in a first part E of the chamber 202. First airflow B is mainly drawn in through perforations 204 in a second part F of the chamber 202. Alternatively, rotor 206 may be horizontal since the influence of gravity is small relative to the centrifugal forces. Optionally, the wall 203 may be sprayed with water intermittently for cleaning.

Further details of the plastics separator 130 shown are contained in International Publication Number WO 2015/050433, which is incorporated herein by reference. A similar plastics separator is sold as the DYNAMIC CYCLONE by DB Technologies, which can process liquid fraction 118 at up to 30% solids. This device can produce separated organic material 132 having 0.1% or less (dry basis) of floatables greater than 2 mm in size. The resulting digestate 108 meets, for example, California regulations for land application and composting.

Figure 4:
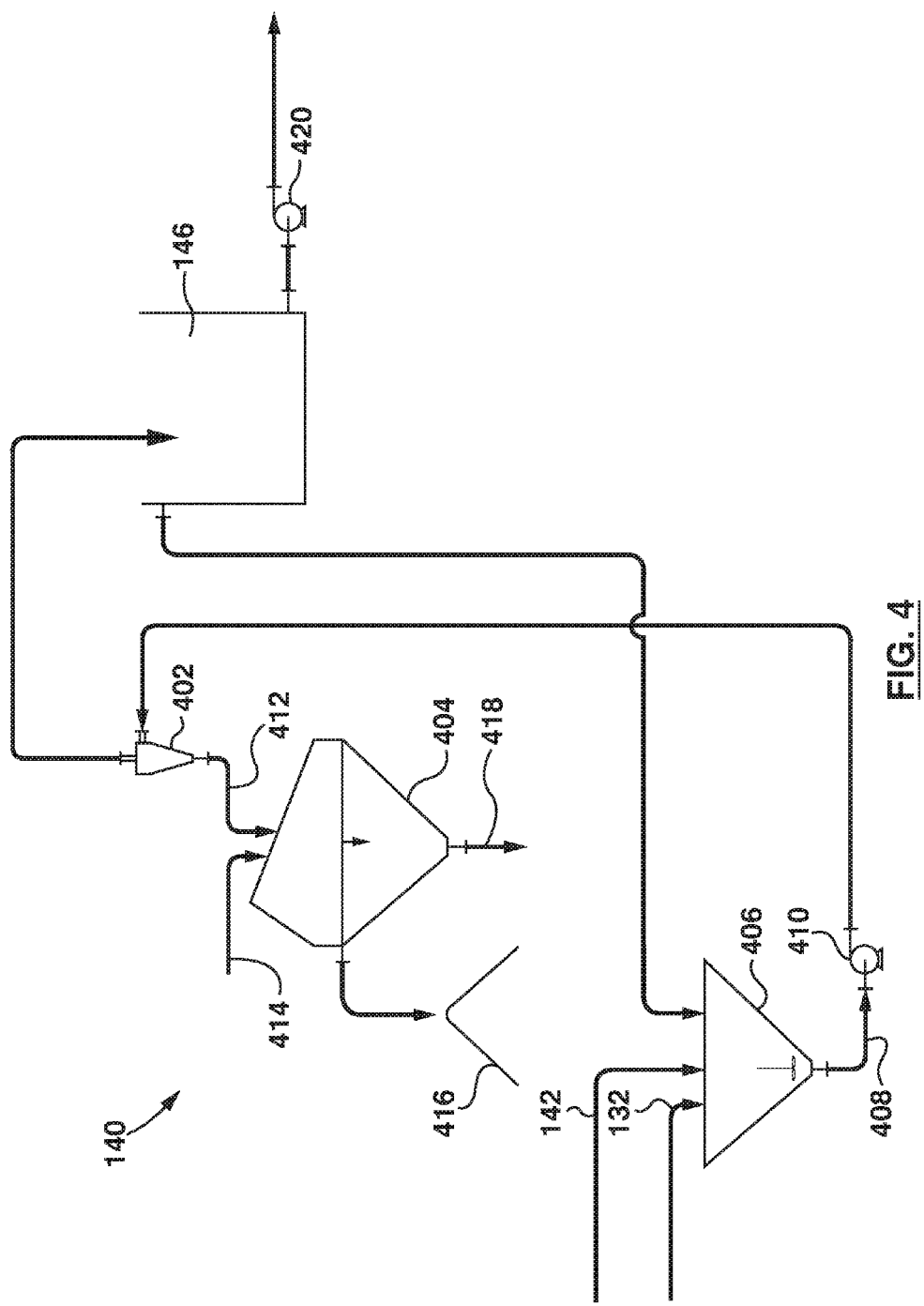
FIG. 4 is a more detailed process flow diagram for the grit removal unit in the FIG. 1.

FIG. 4 shows an example of a grit removal unit 140. Dilutant 142 and separated organic material 132 are mixed in a dilution mixing tank 406. The diluted mixture 408 is fed by slurry pump 410 to the hydrocyclone 402. Grit 412 from the hydrocyclone 402 is sent to s grit washing screen 404 to be washed, for example with plant water 414. Washed grit 416 may be landfilled. Wash water 418 can be wasted or re-used as dilutant 142. Degritted feedstock 146 can be fed, for example by transfer pump 420, to digester 104.

A preferred grit removal unit 140 is the PRO:DEC system by CD Enviro. This system can accept feed at up to 12% solids and will remove 90% particles with a specific gravity of 2 or more that are larger than 100 microns in size from separated organic material 132. This is less grit per unit mass of dry solids than most WWTP sludge and is therefore acceptable for addition into a digester 104 currently in use at a WWTP.

We claim:
1. A process comprising steps of,
   pressing solid waste containing organic material to separate the solid waste into a wet fraction containing organic material that is compressed through perforations in a wall of a compression chamber and a dry fraction;
   diluting the wet fraction;
   degritting the wet fraction; and,
   treating the wet fraction in an anaerobic digester.

2. The process of claim 1 wherein floatables are removed from the wet fraction in a dynamic cyclone.

3. The process of claim 1 wherein degritting is performed with a hydrocyclone.

4. The process of claim 1 wherein the wet fraction is diluted to 8-12% solids.

5. The process of claim 1 wherein the wet fraction is diluted with sludge.

6. The process of claim 1 wherein the wet fraction is co-digested with WWTP sludge.

7. The process of claim 1 wherein floatables are removed from the wet fraction.

8. The process of claim 1 wherein the solid waste is pressed at a pressure of at least 50 bar.

9. The process of claim 1 wherein the solids waste is pressed at a pressure sufficient to rupture cells in the organic material.

10. The process of claim 1 wherein the perforations have a size in the range of 4-10 mm.

11. The process of claim 1 wherein the wet fraction has a solids content of at least 20%.

12. The process of claim 1 wherein the solid waste comprises municipal solid waste and the wet fraction is at least 30% of the solid waste.

13. The process of claim 1 wherein the solid waste comprises source separated organics and the wet fraction is at least 70% of the solid waste.

\* \* \* \* \*